US006395254B1

(12) United States Patent
Sinn et al.

(10) Patent No.: US 6,395,254 B1
(45) Date of Patent: May 28, 2002

(54) CONJUGATE COMPRISING AN ACTIVE AGENT, A POLYPEPTIDE AND A POLYETHER

(75) Inventors: Hannsjörg Sinn, Wiesloch; Wolfgang Maier-Borst, Dossenheim; Hans-Hermann Schrenk, Zeiskamm; Gerd Stehle, Mannheim; Heinz H. Fiebig, Freiburg, all of (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/308,103
(22) PCT Filed: Dec. 20, 1996
(86) PCT No.: PCT/DE96/02487
§ 371 (c)(1),
(2), (4) Date: May 4, 2000
(87) PCT Pub. No.: WO97/23240
PCT Pub. Date: Jul. 3, 1997

(30) Foreign Application Priority Data

Dec. 21, 1995 (DE) .......................... 195 48 114

(51) Int. Cl.[7] .......................... A61K 47/48; A61K 51/06
(52) U.S. Cl. ...................... 424/1.69; 424/9.34; 424/9.4; 424/9.6; 514/2; 530/345; 530/410
(58) Field of Search .................. 424/1.69, 9.34, 424/9.4, 9.42, 9.6, 9.61; 514/2.6; 530/345, 408, 409, 410

(56) References Cited

U.S. PATENT DOCUMENTS 4,318,846 A * 3/1982 Khanna et al. ............. 525/420

FOREIGN PATENT DOCUMENTS

| DE | 40 17 439 | 12/1991 |
| EP | 0 397 307 | 11/1990 |
| WO | WO 94/05203 | 3/1994 |
| WO | WO 94/28940 | 12/1994 |
| WO | WO 96/00079 | 1/1996 |
| WO | WO 96/00088 | 1/1996 |
| WO | WO 96/00588 | 1/1996 |

OTHER PUBLICATIONS

Anzinger et al., 1981, "Peptides with unusual side chains. Synthesis and conformation of poly(ethylene glycol)–polylysine blocks ith mesogenic side groups," *Makromol. Chem. Rapid Commun.* 2(9–10):637–643.

Bogdanov et al., 1995, "Long–circulating blood pool imaging agents," *Adv. Drug Delivery Rev.* 16(2,3):335–348.

Bogdanov et al., 1996, "An Adduct of cis–Diamminedichloroplatinum(II) and Poly(ethylene glycol)poly(L–lysine-)–Succinate: Synthesis and Cytotoxic Properties," *Bioconjugate Chem* 7(1):144–149.

Frank et al., 1994, "Detection of pulmonary emboli by using MR angiography with MPEG–PL–GdDTPA: An experimental study in rabbits," *Americ. J. Roentgenology* 162(5):1041–1046.

Gupta et al., 1995, "Experimental gastrointestinal hemorrhage: Detection with contrast–enhanced MR imaging and scintigraphy," *Radiology* 196(1):239–244.

Gupta et al., 1995, "Inflammation: Imaging with methoxy poly(ethylene glycol)–poly-L–lysine–DTPA, a long circulating graft copolymer," *Radiology* 197(3):665–669.

Yokoyama et al., 1992, "Preparation of micelle–forming polymer–drug conjugates," *Bioconjugate Chemistry* 3(4):295–301.

Zalipsky, 1995, "Chemistry of polyethylene glycol conjugates with biologically active molecules," *Advanced Drug Delivery Reviews* 16(2–3):157–182.

* cited by examiner

*Primary Examiner*—Jeffrey E. Russel
(74) *Attorney, Agent, or Firm*—Pennie & Edmonds LLP

(57) ABSTRACT

The present invention relates to conjugates, comprising an active substance, a polypeptide and a polyether, a process for the production of such conjugates as well as their use.

17 Claims, 2 Drawing Sheets

CONJUGATE COMPRISING AN ACTIVE AGENT, A POLYPEPTIDE AND A POLYETHER

This is a national phase filing of the Application No. PCT/DE96/02487, which was filed with the Patent Corporation Treaty on Dec. 20, 1996, and is entitled to priority of the German Patent Application 195 48 114.3, filed Dec. 21, 1995.

1. FIELD OF THE INVENTION

The present invention relates to conjugates, comprising an active substance, a polypeptide and a polyether, a process for the preparation of such conjugates as well as their use.

2. BACKGROUND OF THE INVENTION

There is a great demand of concentrating active substances at their site of action. This applies particularly to active substances for treating tumors and inflamed tissues, respectively. It is very often tried to obtain the active substance concentration by administration of high amounts of active substance. However, this leads to considerable side-effect in patients, particularly in their livers and kidneys.

Therefore, it is the object of the present invention to provide a possibility of concentrating active substances at their site of action.

3. SUMMARY OF THE INVENTION

The present invention relates to conjugates, comprising an active substance, a polypeptide and a polyether, a process for the preparation of such conjugates as well as their use.

4. BRIEF DESCRIPTION OF THE DRAWINGS

5. DETAILED DESCRIPTION OF THE INVENTION

Figure 1:
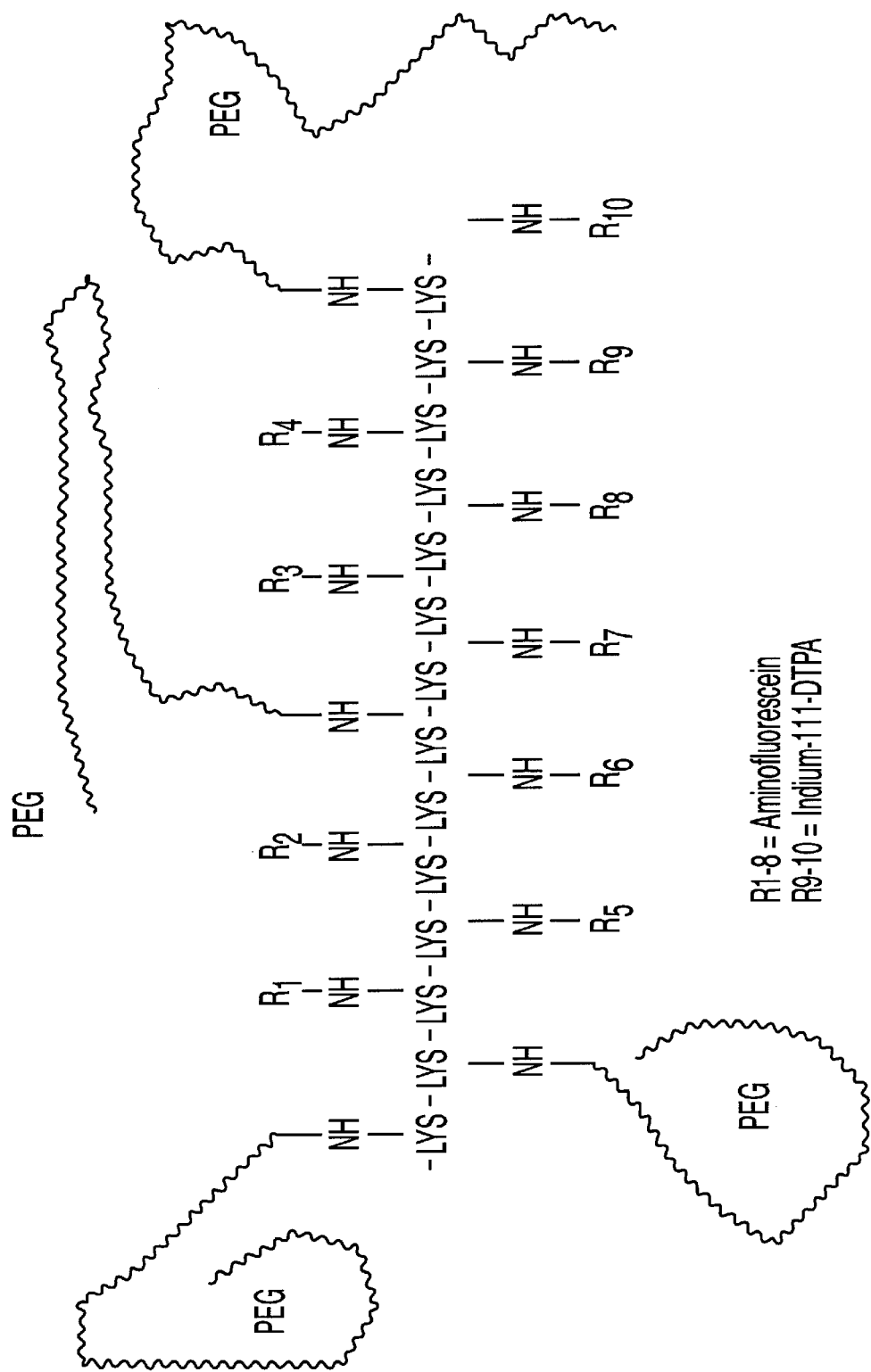
FIG. 1 shows a conjugate according to the invention, comprising polylysine (PL), 4 polyethylene glycols (PEG), 8 aminofluoresceins (AF1) and 2 diethylenetriaminepentaacetates (DTPA) labeled with $^{111}$In, AF1 being linked via cyanuric chloride to free amino groups of PL, and DTPA being linked to PL via an acid amide bridge (SEQ ID NO:1).

It is the object of the present invention to provide a possibility of concentrating active substances at their site of action. According to the invention this is achieve by the subject matters defined in the claims.

Thus, the subject matter of the present invention relates to a conjugate comprising an active substance, a polypeptide and a polyether.

The expression "active substance" comprises substances of any kind which can be used for treating and/or diagnosing a disease, particularly a tumoral disease and/or an inflammatory disease. Examples of such substances are chemotherapeutic agents, photoactive substances, radioactive substances, fluorescence-capable substances or substances capable of emitting fluorescence, substances for fluoro-nuclear magnetic resonance spectroscopy, substances as radiosensitizers and/or substances having binding sites for metallic compounds. Examples of the chemotherapeutic agents are virostatics, antiprotozoals, cytostatic agents and antibiotics. Representatives thereof are e.g. doxorubicin, daunorubicin, tetracyclines, antimetabolites such as methotrexate, and derivatives thereof. Examples of photoactive substances are porphyrins, such as o-, m- and/or p-tetracarboxyphenylporphyrin (TCPP), chlorins and bacteriochlorins. An example of the radioactive substance is a tyrosine labeled with radioactive iodine. Examples of the substances capable of emitting fluorescence are fluorescent dyes, such as fluorescein, aminofluorescein (AF1) as well as derivatives and analogues thereof. Examples of the substance for fluoro-nuclear magnetic resonance spectroscopy are polyfluorocarboxylic acids such as trifluoroacetic acid. An example of the radiosensitizer substance is m-aminobenzoic amide. Examples of the substances having a binding site for metallic compounds are substances which include hydroxyl, carbonyl or carboxyl groups. They may have one or more binding sites, preferably at least 2, more preferably 3 to 6. If several binding sites are present, they may be the same or differ from one another. Examples of the substances having binding sites for metallic compounds are ethylenediaminetetraacetate, diethylenetriaminepentaacetate (DTPA), triethylenetetraaminehexaacetate, alizarin and derivatives thereof. Substances having binding sites for metallic compounds favorably have a detectable metallic compound which may contain or consist of one or more detectable metals and/or metal ions. Examples of such metals are Zn, Cu, Co, Fe, Ni, Pt, Gd and In, which are preferably bivalent or trivalent, $Gd^{3-}$ being especially preferred. The metals and/or metal ions may be radioactive, such as $^{111}$In.

One or more of the above active substances may be present in the conjugate according to the invention. If several are present, they may be the same or differ from one another.

The expression "polypeptide" comprises polypeptides of any kind which have up to 50 amino acids, preferably 7 to 30 amino acids, especially preferably 10 to 30 amino acids. The polypeptide may have equal or different amino acids. The amino acids are preferably those having amino, carboxyl or phenolic OH-groups in the side groups. They may be non-naturally occurring and/or naturally occurring amino acids such as lysine, tyrosine, asparaginic acid and glutamic acid. Especially preferred polypeptides are polylysine (PL) 1, polytyrosine, polyasparaginic acid and polyglutamic acid.

A person skilled in the art is familiar with the above polypeptides. They can be purchased or be prepared by known techniques, e.g. the Merriefield technique.

A polyether is present in the conjugate according to the invention. It protects the conjugate particularly from excretion via the kidneys and provides it with a good water solubility. The polyether preferably has a molecular weight of 2,000 to 5,000 daltons. The polyether may be etherified or esterified at the terminal hydroxyl group by a $C_1$–$C_{12}$ alkyl group, particularly methyl group. The polyether is preferably a polyethylene glycol (PEG), such as methoxypolyethylene glycol, and is bound to the polypeptide via active groups such as methoxypolyethylene glycol-p-nitrophenylcarbonate, methoxypolyethylene glycol succinimidylsuccinate, methoxypolyethylene glycol tresylate, methoxypolyoxyethyleneamine, methoxypolyoxyethylene-carboxylic acid and methoxypolyoxyethyleneimidazolcarbonyl.

The conjugate according to the invention may also contain several of the above polyethers, preferably 2 to 6. They may be the same or differ. If several polyethers are present, the sum of the molecular weights thereof is favorably 10,000 to 50,000 daltons.

In the conjugate according to the invention, the individual components can be linked directly, e.g. covalently, via an acid amide or acid ester bond, or indirectly via a linker such as cyanuric chloride. Both the active substance and the polyether are linked preferably to the polypeptide.

The above components of the conjugate according to the invention are given as educts. Therefore, they are present in derivatized form in the conjugate according to the invention.

Examples of conjugates according to the invention are indicated in FIG. 1 and Example 1.

A process for the preparation of an above conjugate is also provided according to the invention. In such a process, the polypeptide, the active substance and the polyether are linked with one another as usual, preferably covalently. Reference is made to the preparation of a conjugate according to the invention in Example 1.

Conjugates according to the invention distinguish themselves by concentrating well in tumors and tissues damaged by inflammatory diseases. In addition, they can be charged with the most differing active substances, particularly at the same time, without begin immunogenic. This is a great advantage over prior art conjugates which often, when several active substances are simultaneously present, cause undesired immune responses in patients. Thus, the conjugates according to the invention are well suite for treating diseases, particularly tumoral and inflammatory diseases.

Furthermore, the conjugates according to the invention are well suited for the diagnosis of diseases, particularly tumoral and inflammatory diseases. For example, the active substance of conjugates according to the invention may be a substance capable of emitting fluorescence. These conjugates are given to the tumor patient e.g. before an operation. The conjugates according to the invention then concentrate in the tumor. During the operation, the substance capable of emitting fluorescence can be stimulated by light, e.g. a UV lamp, to emit fluorescence. Thus, healthy tissue can be distinguished from tumor tissue.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

6. EXAMPLES a. Example 1

Preparation of a Conjugate According to the Invention, Comprising PL, 8 AF1, 2 DTPA and 4 Methoxypolyethylene Glycols (MPEG)

50 mg of 5([4,6-dichlorotriazine-2-yl]amino) fluorescein (AF1, MW 531.7; Sigma) were dissolved in 4 ml of dimethylsulfoxide (DMS) and added to 100 mg of polylysine (PL-MW~1000 D, Sigma), dissolved in 2 ml DMSO and 2 ml of distilled water. Then 1 ml 0.34 M $NaHCO_3$ was added, and the slightly turbid solution was allowed to stand or about 30 min.

1 g of methoxypolyethylene glycol (MPEG)—nitrophenylcarbonate was dissolved in 10 ml of dioxan and added to the above AF1-PL solution. 50 µl of 1 N NaOH were added thereto. The conversion was terminated after about 48 hours. PL-AFL-$MPEG_4$ was obtained. Unwanted accompanying substances were separated by ultrafiltration (YM 10). The molecular weight was determined by means of GPC as usual.

PL-AF1-$MPEG_4$ was reacted with diethylenetriaminepentaacetic acid (DTPA) which was labeled with $^{111}$In for the nuclear-medical use or with gadolinium (Gd) as tumor-penetrating MR contrast agent, as follows:

Diethylenetriaminepentaacetic acid (DTPA) was dissolved by heating to a concentration of 20 mg/ml in DMSO. After cooling the clear solution to room temperature, 1.5 to 2 time the molar amount of N,N'-dicyclohexylcarbodiimide (DCC) and 5 times the molar amount of N-hydroxysuccinimide (HS1) were added. After a reaction time of about 14 to 15 h, the formation of the succinimidyl ester (DTPA-SE) was completed. It was used for the subsequent linkage to PL-AF1-$MPEG_4$.

For this purpose, the above solution of DTPA-SE was added very slowly and with constant stirring to the above PL-AFL-$MPEG_4$ solution purified by ultrafiltration, the initially clear solution becoming turbid by excess and unreacted DCC and still dissolved di-cyclohexylurea (DCCH) which are both insoluble in aqueous solution. Having terminated the addition of DTPA-SE, the reaction mixture was stirred for full reaction at room temperature for another 60 minutes. Thereafter, the turbid matter was separated via a sterile filter unit (Millipore, Stericup-CV, 0.22 µm Low Binding Duropore Membrane) and the low-molecular water-soluble components (DMSO, HSI and unbound DTPA) were separated by ultrafiltration via a membrane with 10 kD exclusion limit (Amicon). Analytical purity was controlled by means of HPLC. The PL-AFL-$MPEG_4$-$DTPA_2$ (A) conjugate according to the invention was obtained.

For labeling (A) with $^{111}$In, 10 to 20 µl of a 0.2 M Na-citrate solution were added to 185 Mbq $^{111}$In (5 mCi) charged as 0.1 M of hydrochloric acid solution of $^{111}$InCl$_3$ having a low carrier content. For this purpose, about 5 mg (A), dissolved in 1 to 2 ml 0.17 M $NaHCO_3$ were added. Thereafter, the reaction mixture was separated by ultrafiltration from unbound $^{111}$In and citrate. For this purpose, the reaction volume was filled up to 2 ml and inserted in a disposable ultrafiltration unit (Centricon C 30, Amicon), the separation of the low-molecular contaminations taking place by centrifugation in a rotor which can be inclined by 45°. (A) labeled with $^{111}$In was obtained.

The charging of (A) with Gd was carried out in a manner the same as the labeling with $^{111}$In, only greater substances amounts being required.

b. Example 2

Absorption of a Conjugate According to the Invention in Tumor Tissue a) Rats having a Walker 256 carcinosarcoma were given intravenously about 70 µCi (2 mg/kg) of the conjugate of FIG. 1 according to the invention. The distribution of the conjugate in the rats was shown by scintiscanning after 5 minutes, 1, 3, 24 and 48 hours. The result is shown FIG. 2.

Figure 2:
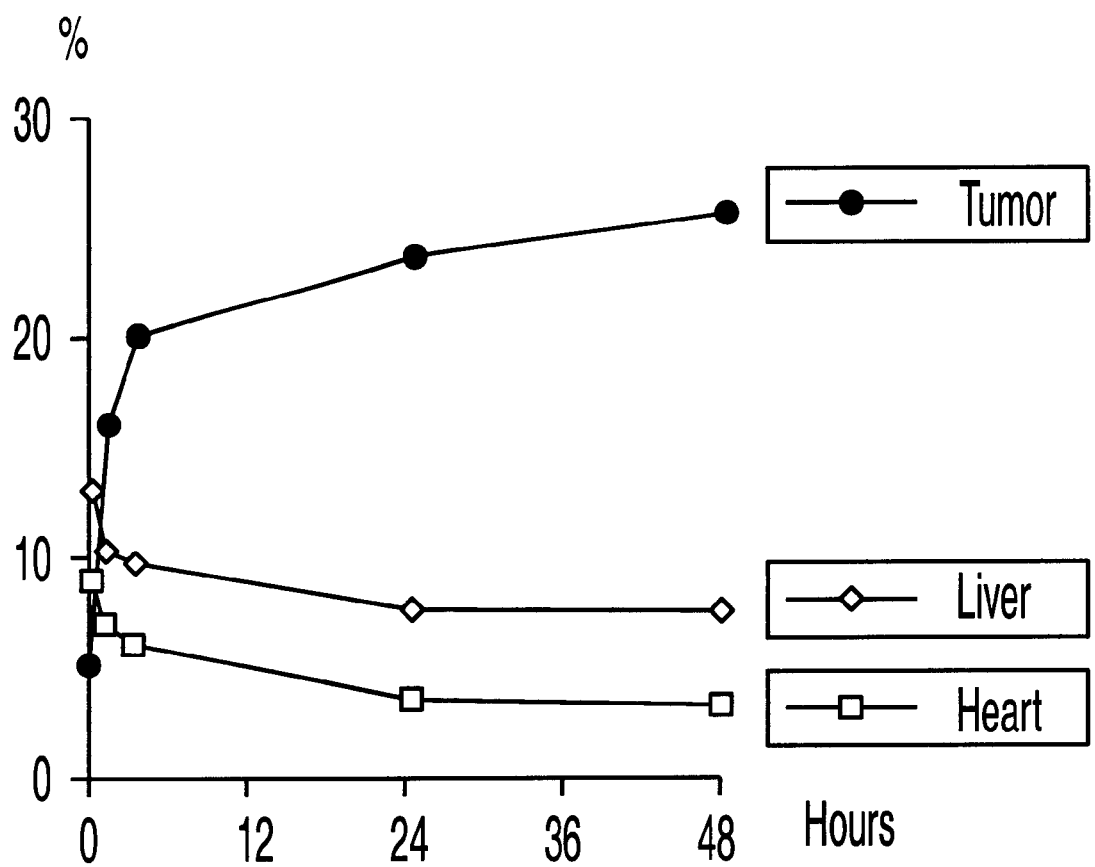
FIG. 2 shows the distribution of the conjugate of FIG. 1 according to the invention, measured by means of scintiscanning, in tumor tissue.

FIG. 2 discloses that the conjugate according to the invention concentrates in the tumor but not in the cardiac or liver region.

b) The above rats were killed after 48 hours, and the radioactivity distribution in the organs was determined. The results are shown in Table 1.

Table 1 discloses that the conjugate according to the invention concentrates in the tumor.

TABLE 1

Distribution of the conjugate of FIG. 1 according to the invention in the blood, in certain organs and in the tumor of a rat. 30% of the radioactivity left in the body is found in the tumor which only constitutes 4.8% of the body weight.

|   | Weight/volume | amount of Conjugate (μCi) | Moiety (%) |
|---|---|---|---|
| rat | 243.0 | 27.5 | 100% |
| blood | 15.4 ml | 1.32 | 4.8% |
| tumor | 11.2 g | 8.50 | 30.9% |
| skin | 40.2 g | 0.75 | 2.9% |
| spleen | 0.55 g | 0.23 | 0.8% |
| kidneys (together) | 2.38 g | 2.60 | 9.4% |
| liver | 10.71 g | 2.82 | 10.2% |
| gastrointestinal tract | 13.30 g | 1.43 | 0.5% |

All references cited within the body of the instant specification are hereby incorporated by reference in their entirety.

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide
<221> NAME/KEY: SITE
<222> LOCATION: 1,2,7,13
<223> OTHER INFORMATION: Lysine modified with p olyethylene glycol
<221> NAME/KEY: SITE
<222> LOCATION: 3,4,5,6,8,9,10,11
<223> OTHER INFORMATION: Lysine linked via cyan uric chloride to
      aminofluorescein (AF1)
<221> NAME/KEY: SITE
<222> LOCATION: 12,14
<223> OTHER INFORMATION: Lysine linked via an acid amide bridge to
      diethylenetriaminepentaacetate (DTPA) lab eled with
      In-111

<400> SEQUENCE: 1

Xaa Xaa Xaa Xaa Xaa Xaa Xaa Xaa Xaa Xaa X aa Xaa Xaa Xaa
1               5                   10
```

What is claimed is:

1. A conjugate for diagnosing or treating a tumor or an inflammatory disease in a subject comprising an active substance, a polypeptide and one to six polyethers, wherein each polyether is attached to the polypeptide via a side chain of the polypeptide, and the conjugate concentrates in the subject in the tumor or in a tissue damaged by the inflammatory disease.

2. The conjugate of claim 1, wherein the active substance is a substance useful for diagnosing a tumoral disease in a subject, and the conjugate concentrates in a tumor.

3. The conjugate of claim 1, wherein the active substance is a chemotherapeutic agent, a photoactive substance, a radioactive substance, a substance capable of emitting fluorescence, a substance for fluoro-nuclear magnetic resonance spectroscopy, a substance as radiosensitizer or a substance having a binding site for metallic compounds.

4. The conjugate of claim 1, comprising several active substances.

5. The conjugate of claim 1, wherein the polypeptide consists of about 7 to about 30 amino acids.

6. The conjugate of claim 1, wherein the polypeptide comprises amino acids which have amino, carboxyl or phenolic OH groups in the side chains.

7. The conjugate of claim 1, wherein the polypeptide consists of naturally occurring amino acids.

8. The conjugate of claim 7, wherein the amino acids are selected from the group consisting of lysine, tyrosine, asparaginic acid and glutamic acid.

9. The conjugate of claim 8, wherein the polypeptide is polylysine, polytyrosine, polyasparaginic acid or polyglutamic acid.

10. The conjugate of claim 1, wherein the polyether has a molecular weight of 2,000 to 5,000 daltons.

11. The conjugate of claim 1, wherein the polyether is a polyethylene glycol.

12. A process for the preparation of a conjugate of claim 1, wherein the active substance, the polypeptide and the polyether are bonded covalently with one another.

13. A method for treating a tumoral disease or an inflammatory disease, comprising administering the conjugate of claim 1.

14. A method for diagnosing a tumoral disease or an inflammatory disease, comprising administering the conjugate of claim 1.

15. The conjugate of claim 1, wherein the active substance is a substance useful for treating a tumoral disease in a subject, and the conjugate concentrates in a tumor.

16. The conjugate of claim 1, wherein the active substance is a substance useful for diagnosing an inflammatory disease in a subject, and the conjugate concentrates in a tissue damaged by an inflammatory disease.

17. The conjugate of claim 1, wherein the active substance is a substance useful for treating an inflammatory disease, and the conjugate concentrates in a tissue damaged by an inflammatory disease.

* * * * *

UNITED STATES PATENT AND TRADEMARK OFFICE
CERTIFICATE OF CORRECTION

PATENT NO.     : 6,395,254 B1                                                Page 1 of 1
DATED          : May 28, 2002
INVENTOR(S)    : Hannsjörg Sinn et al.

It is certified that error appears in the above-identified patent and that said Letters Patent is hereby corrected as shown below:

<u>Title page, Item [54] and Column 1, line 2,</u>
Please replace the word "AGENT" with -- SUBSTANCE --;
Item [86], PCT PUB No. please replace "May 4, 2000" with -- March 24, 2000 --;

Signed and Sealed this

Twenty-sixth Day of November, 2002

*Attest:*

*Attesting Officer*

JAMES E. ROGAN
*Director of the United States Patent and Trademark Office*